United States Patent
Gunderson

(10) Patent No.: US 7,955,370 B2
(45) Date of Patent: Jun. 7, 2011

(54) STENT DELIVERY SYSTEM

(75) Inventor: Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1214 days.

(21) Appl. No.: 10/912,917

(22) Filed: Aug. 6, 2004

(65) Prior Publication Data

US 2006/0030923 A1 Feb. 9, 2006

(51) Int. Cl.
*A61F 2/06* (2006.01)
(52) U.S. Cl. .................................................. 623/1.11
(58) Field of Classification Search .................. 623/1.15, 623/1.11; 606/194
See application file for complete search history.

(56) References Cited

U.S. PATENT DOCUMENTS

| | | | |
|---|---|---|---|
| 5,681,345 A | 10/1997 | Euteneuer | 623/1.11 |
| 5,690,644 A * | 11/1997 | Yurek et al. | 623/1.11 |
| 5,788,707 A | 8/1998 | Del Toro et al. | 623/1.11 |
| 6,066,155 A | 5/2000 | Amann et al. | 606/192 |
| 6,096,045 A | 8/2000 | Del Toro et al. | 606/108 |
| 6,221,097 B1 | 4/2001 | Wang et al. | 623/1.11 |
| 6,331,186 B1 | 12/2001 | Wang et al. | 623/1.11 |
| 6,342,066 B1 | 1/2002 | Toro et al. | 623/1.11 |
| 6,350,277 B1 | 2/2002 | Kocur | 623/1.11 |
| 6,443,880 B2 | 9/2002 | Blais et al. | 492/16 |
| 6,478,814 B2 | 11/2002 | Wang et al. | 623/1.2 |
| 6,942,682 B2 * | 9/2005 | Vrba et al. | 606/198 |
| 2005/0070997 A1 * | 3/2005 | Thornton et al. | 623/1.46 |

FOREIGN PATENT DOCUMENTS

| | | |
|---|---|---|
| JP | 11313893 | 11/1999 |
| WO | 9205829 | 4/1992 |
| WO | WO 96/32078 | 10/1996 |
| WO | WO 01/78627 | 10/2001 |
| WO | WO 01/78627 A1 * | 10/2001 |
| WO | WO 02/38084 | 5/2002 |

\* cited by examiner

*Primary Examiner* — Melanie Tyson
(74) *Attorney, Agent, or Firm* — Vidas, Arrett & Steinkraus, P.A.

(57) ABSTRACT

A medical device includes a catheter having a catheter shaft, a sheath and a rolling membrane. The sheath is being disposed about the catheter shaft and is longitudinally moveable relative thereto. A distal portion of the sheath defines a stent retaining region. The sheath is moveable between an extended position and a retracted position, wherein in the extended position the retaining region is disposed about a stent receiving region of the catheter shaft, and in the retracted position the sheath is removed from the stent receiving region. End regions of the rolling membrane are respectively engaged to a distal end of the sheath and a portion of the shaft proximal to the stent receiving region respectively.

19 Claims, 5 Drawing Sheets

STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, vena cava filters, vascular implants, and similar implantable medical devices, collectively referred to hereinafter as stents, are radially expandable endoprostheses which are typically intravascular implants capable of being implanted transluminally and enlarged radially after being introduced percutaneously. Stents are typically mounted onto a catheter assembly for deployment within a body lumen. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. Nos. 5,681,345; 5,788,707; 6,066,155; 6,096,045; 6,221,097; 6,331,186; 6,342,066; 6,350,277; 6,443,880; 6,478,814 and U.S. patent application Ser. No. 09/664,268 entitled Rolling Socks and filed Sep. 18, 2000.

In some systems for the delivery of a self-expanding stent, the stent is deployed by a pull back sheath system. When the stent is constrained within the system, the stent is exerting a force onto the inside diameter (ID) of the outer shaft or pull back sheath. The frictional interface between the stent and sheath may cause the sheath to negatively interact with the stent as the sheath is retracted during deployment. Lubricious coatings may be used to aid in reducing the frictional interface between the stent and sheath. In some cases, particularly those involving longer stents and thus greater frictional forces, the forces may be to great for the lubricant to compensate for. As a result, in some systems the frictional forces involved will prevent the catheter from being capable of properly deploying a stent of a desired length.

Excess frictional interaction between the stent and sheath is of particular concern in systems deploying a stent that incorporates one or more therapeutic coatings thereon, as the coatings may be adversely affected by the frictional interface between the sheath and stent, particularly during sheath retraction.

The present invention seeks to address these and/or other problems by providing catheter assemblies with a variety of embodiments and features which improve sheath retraction and stent deployment characteristics.

All U.S. patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a co-axial stent delivery system having a roll back inner membrane and an outer pull-back sheath. Prior to delivery of the stent the inner membrane is disposed directly about the stent and the pull back sheath is disposed about the membrane. A distal end of the membrane is engaged to a distal portion of the sheath and a proximal end of the membrane is engaged to a portion of the inner catheter shaft proximal of the stent retaining region of the catheter assembly. When the pull back sheath is retracted the membrane will be drawn along with the sheath and will roll back proximally along the length of the stent until the stent is fully exposed and deployed.

In at least one embodiment a lubricious coating is positioned between the roll back membrane and the sheath.

In at least one embodiment a lubricious coating is positioned between the stent and the roll back membrane.

In at least one embodiment a fluid is present in a lumen or chamber defined by the roll back membrane and the sheath. The fluid may be sufficiently pressurized to maintain a gap between the membrane and sheath during retraction.

In at least one embodiment the invention is directed to a tri-axial system wherein a secondary lumen is formed between an intermediate shaft or mid-shaft and the inner shaft proximal to the stent retaining region. The proximal end of the roll back membrane may be engaged to a distal portion of the mid-shaft, thereby extending the secondary lumen into the stent retaining region of the catheter. The secondary lumen provides a flush path through which a fluid may be transported to the stent retaining region during or prior to delivery of the stent.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
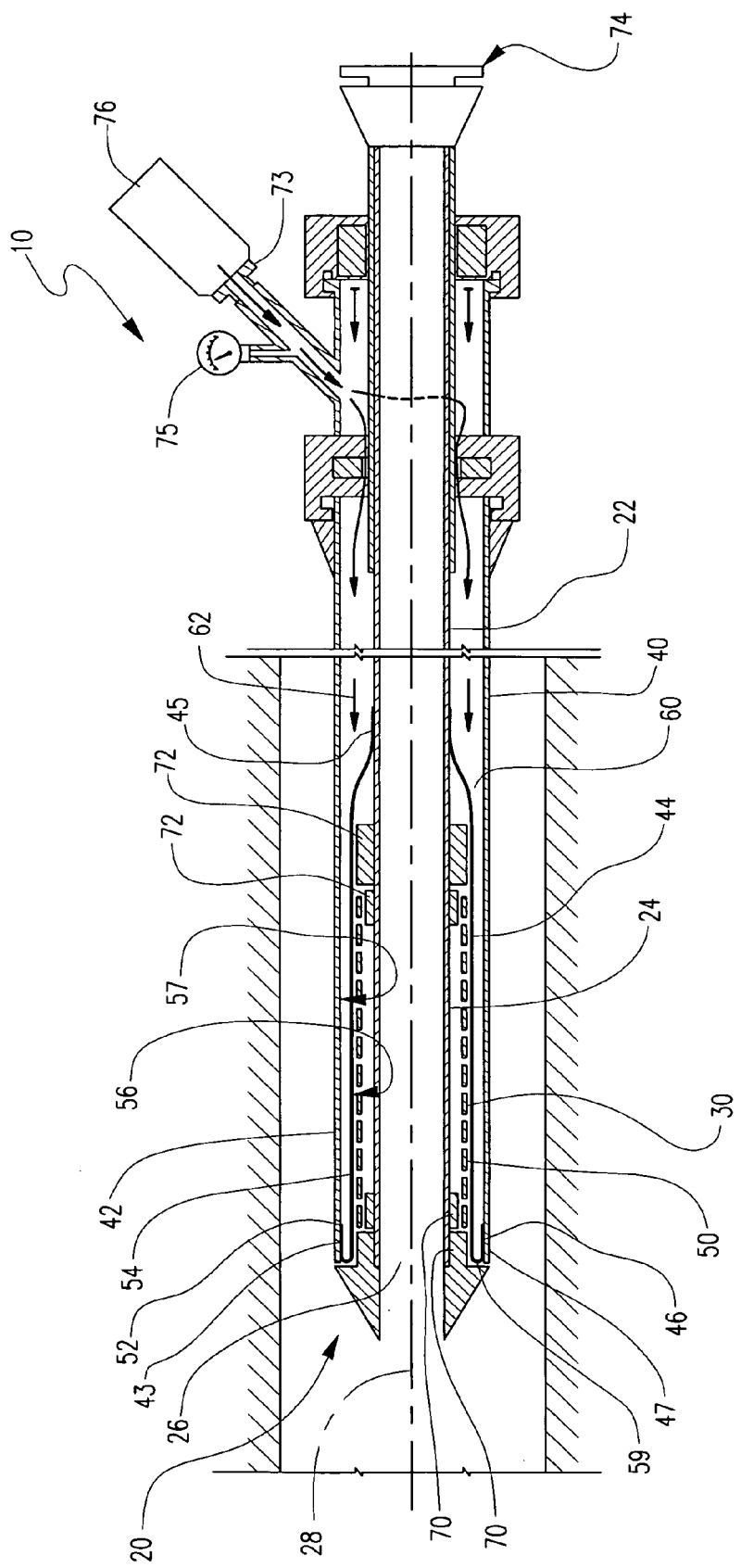
FIG. 1 is a schematic longitudinal cross-sectional view of distal and proximal portions of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
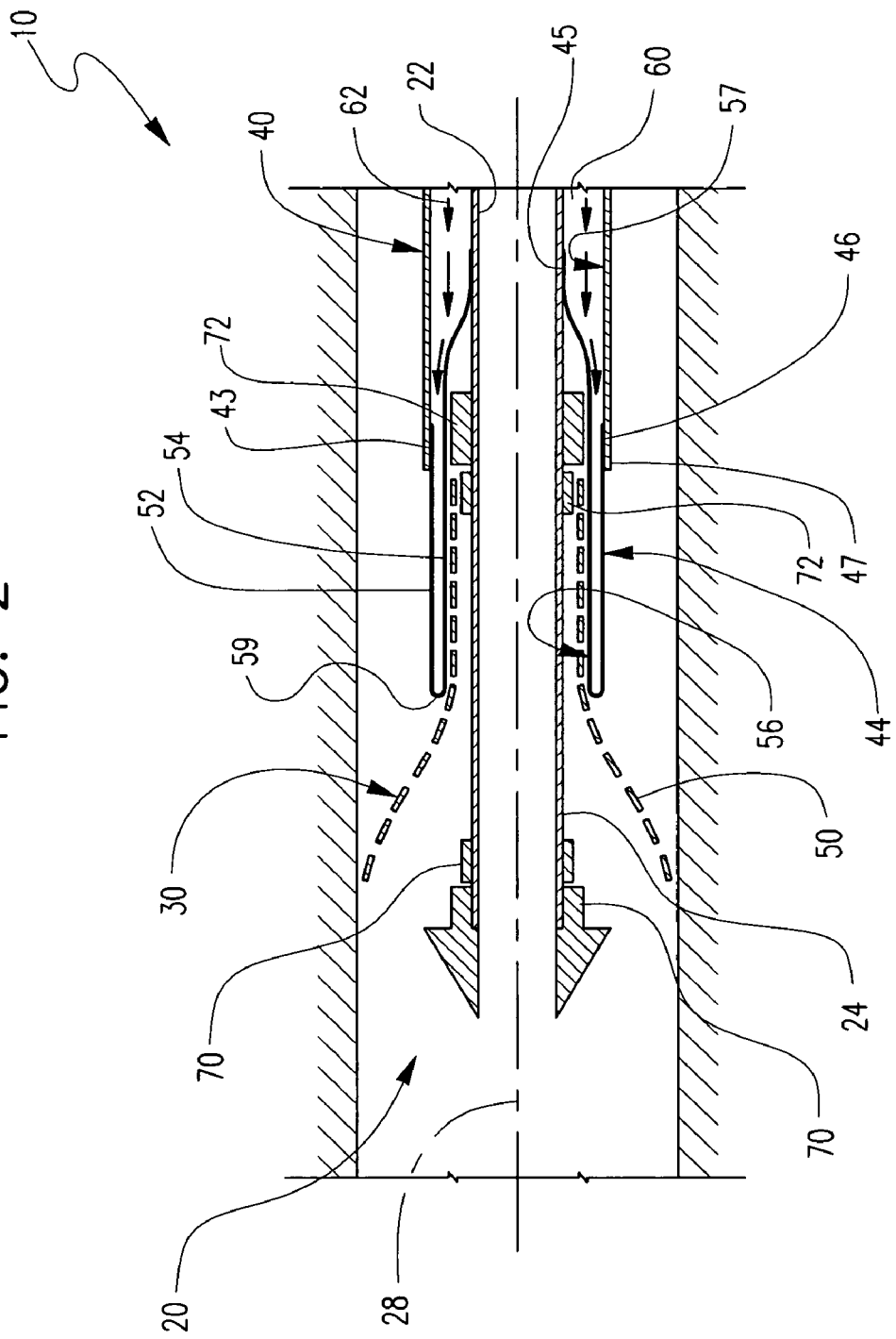
FIG. 2 is a longitudinal cross-sectional view of the distal portion of the embodiment depicted in FIG. 1 shown during retraction of the membrane and sheath.
Figure 3:
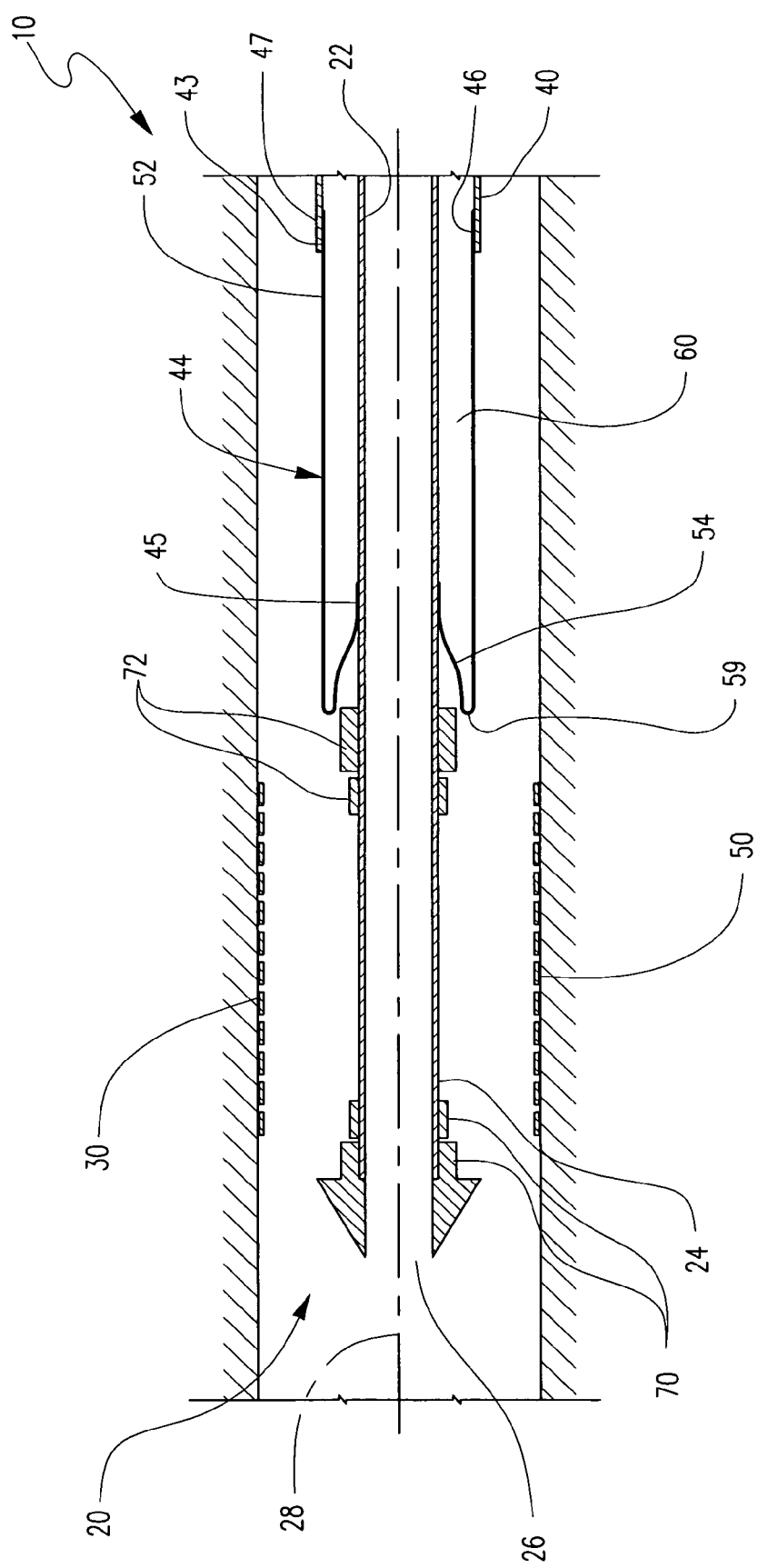
FIG. 3 is a longitudinal cross-sectional view of the embodiment depicted in FIG. 1 shown with the membrane and sheath fully retracted from the stent.

In at least one embodiment, an example of which is shown in FIGS. 1-3, a delivery system 10, is depicted which includes a catheter 20 which is configured to deliver a stent 30, which in at least one embodiment is a self-expanding stent.

Catheter 20 includes a catheter shaft or inner shaft 22, a portion of which defines a stent receiving region 24. Catheter shaft 22 may further define a guidewire lumen 26 through which a guidewire 28 may be passed in order to advance the catheter to a predetermined position in a body lumen or vessel. Alternatively, the shaft 22 may be configured as a fixed-wire catheter.

The catheter 20 may be any type of catheter desired and in some embodiments may include a catheter shaft 22 having a substantially hexagonal cross-sectional shape, such as is described in the Inventor's concurrently filed application Ser. No. 10/912,845 entitled Medical Device Delivery System, the entire content of which is incorporated herein by reference.

As shown in FIG. 1, a stent 30 may be a self-expanding stent which is disposed about the stent receiving region 24 of the catheter shaft 22. In some embodiments the stent may be at least partially constructed from one or more of the following shape memory materials: nitinol, shape-memory polymer(s), etc., but may include other material or materials as well. In at least one embodiment the stent is at least partially constructed of stainless steel, cobalt, chromium, titanium, nickel, and any combinations or alloys thereof.

In some embodiments the stent includes one or more areas, bands, coatings, members etc that is (are) detectable by imaging modalities such as X-Ray, MRI or ultrasound. In some embodiments at least a portion of the stent 30 is at least partially radiopaque.

In some embodiments the stent 30 may include one or more therapeutic and/or lubricious coatings 50 applied thereto.

A therapeutic agent may be included with the stent. In some embodiments the agent is placed on the stent in the form of a coating 50. In at least one embodiment the coating 50 includes at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

In some embodiments the at least a portion of the stent may include a stent covering. The covering may be constructed of a variety of materials such as Dacron, PTFE, etc. In at least one embodiment the covering comprises at least one therapeutic agent.

In the various embodiments described herein the stent 30 is preferably configured to be at least partially self-expanding or have self-expanding characteristics. As used herein the term "self-expanding" refers to the tendency of the stent to return to a predetermined diameter when unrestrained from the catheter, such as in the manner depicted in FIGS. 1-3. In the present embodiment when the stent is disposed about the stent receiving region 24 of the catheter shaft 22, the stent is restrained in its reduced diameter or pre-delivery configuration by retractable sheath 40 which is disposed about the entire length of the stent 30 prior to delivery.

The sheath 40 includes a stent retaining region 42, which refers to that region of the sheath 40 which is disposed about the stent 30 prior to delivery. Engaged to a portion of the stent retaining region 42 is a roll back sleeve or membrane 44. To deliver the stent 30, the sheath 40 is retracted proximally, which causes the membrane 44 to roll back off of the stent in the manner illustrated in FIGS. 2-3.

In some embodiments the membrane 44 comprises a distal end region 43 and a proximal end region 45. The proximal end region 45 is engaged to a portion of the inner shaft 22 proximal to the stent receiving region 24.

The distal end region 43 of the membrane is engaged to a distal end portion 47 of the sheath 40 at an engagement region 46. The membrane 44 and sheath 40 may be engaged together by any mechanism and/or configuration desired. For example region 43 and portion 47 may be engaged together by chemical, or adhesive welding or bonding, fusion or heat welding, ultrasonic welding, etc.; they may be mechanically engaged along complementary surfaces; an additional component such as a fastener or other device may be utilized to secure the components together, etc. In some embodiments the membrane 44 and the sheath 40 may be butt-welded or joined, or lap-welded or joined.

As is shown in FIG. 1, in at least one embodiment the distal end region 43 of the membrane 44 can be folded back upon itself to engage the distal end region of the sheath 40. This results in effectively engaging the inside surface (i.e. that surface which at its proximal extent is in contact with the exterior of the stent) 56 of the membrane 44 to the inside surface 57 of the sheath 40. This folded arrangement provides the membrane 44 with a continuous bend region 59 which not only aids in providing the membrane 44 with the tendency to roll back upon itself rather than buckle or slide during retraction, but also aids in the formation of a potential gap between the membrane 44 and sheath 40 proximal to their engagement region 46.

As illustrated in the various figures this "gap" functions as a fluid lumen or chamber 60 into which a fluid, represented by arrows 62, from a fluid source 76 (such as a syringe, etc) may be transported via a fluid port 73 at the proximal end region 74 of the catheter 20. The proximal end region 74 of the catheter may have any handle configuration desired and may have any desired mechanism for regulating the flow of fluid 62 into and/or out of the chamber 60. In at least one embodiment the catheter 20 may include a pressure gauge 75 or other mechanism for monitoring and regulating to volume, flow rate, and/or pressure of the fluid 62 with in the catheter.

In a proximal region of the catheter the fluid chamber 60 acts as a lumen to transport the fluid distally into the area of the stent retaining region of the sheath 40. The proximal portion of the chamber or lumen 60 is defined by the sheath 40 and the inner shaft 22. As indicated, the distal region of the chamber 60 is defined by the sheath 40 and the membrane 44.

While the fluid 62 may be in the form of a coating, such as a lubricious hydrogel, saline, etc. which aids in reducing the potential frictional interactions between the sheath 40 and membrane 44, in some embodiments however a volume of fluid 62 may be injected into the lumen 60 under a predetermined pressure which is maintained during the stent delivery process depicted in FIGS. 2 and 3. The use of fluid 62 under pressure keeps the gap between the sheath 40 and membrane 44 open throughout the retraction process effectively minimizing any sliding friction therebetween, as well as limiting the frictional forces resulting from the stent's tendency to push outward against the sheath 40. As illustrated in FIG. 2, in addition to the above, the pressure exerted by the fluid 62 against the membrane 44 maintains the membrane 44 over the stent and provides the folded over membrane 44 with a turgid-like state sufficient to retain a portion of the stent 30 thereunder in the reduced state until the membrane 44 is retracted.

In some embodiments the pressure exerted by fluid 62 on the membrane 44 may be monitored and regulated by the pressure gauge 75, such as is shown in FIG. 1. A desired pressure of fluid 62 may be maintained within the chamber 60 by the use of any of a variety of devices such as stop-cocks, relief valves, etc.

When the sheath 40 and the membrane 44 are fully withdrawn from about the stent 30, the stent is delivered into a desired location within a body lumen or vessel.

Because the sheath 40, and particularly the distal portion or stent retaining region 42 of the sheath, is configured to retain the stent 30 in its reduced or pre-delivery diameter, in some embodiments at least the stent retaining region 42 of the sheath 40 is constructed to have sufficient hoop strength to prevent the stent from expanding off of the stent receiving region 24 until the sheath 40 is retracted. At least the stent retaining region 42 of the sheath 40 may be constructed from one or more of the materials including but not limited to: polymer materials such as Pebax, Hytrel, Arnitel, Nylon, etc. In at least on embodiment the stiffness of the sheath 40 can be varied by changing the polymer durometers from the proximal end to the distal end by any manner desired.

In some embodiments the sheath 40 comprises a multi-layer construction wherein one or more materials are layered, braided or otherwise combined to form the sheath 40.

In some embodiments the sheath 40 may be provided with a PTFE liner or such a liner may be absent. Where a liner is provided, an inner PTFE liner may be braided with an additional polymer as desired.

In at least one embodiment the sheath 40 is of the same or similar construction as a guide catheter.

In some embodiments the sheath 40 is at least partially constructed of a clear polymer. Such a clear polymer may be used to provide the sheath 40 with a substantially clear distal end region. The clear distal end would allow for viewing the stent or implant device in a constrained state under the sheath.

In at least one embodiment the inside of the sheath is coated for enhanced lubricity.

While the stent retaining region 42 of the sheath 40 is typically constructed to have greater hoop strength than the membrane 44, the sheath may be less flexible than the membrane 44 as well.

The membrane 44 may be at least partially constructed of one or more of a variety of flexible materials such as including but not limited to: Pebax, PET, Nylon, POC, Polyurethane, etc. In some embodiments the material of the membrane 44 may include those which are nanoceramic for added durability. In some embodiments the membrane 44 is at least partially made from one or more polymers with surface alterations such as plasma treatment for enhanced lubricity. In at least one embodiment the membrane 44 comprises one or more layers of material. In at least one embodiment one or both sides of the membrane 44 are coated and/or provided with surface enhancements. Coating can include silicones or other substances to enhance lubricity.

In at least one embodiment the membrane 44 is at least partially constructed from those materials from which medical balloons are known to be manufactured from. Such membrane material may be blown or extruded to any dimensions desired. The wall thickness of the membrane may vary and may be about 0.001 inches to no more than about 0.005 inches thick. In at least one embodiment the thickness of the membrane is less than about 0.001 inches.

In the embodiments depicted in FIG. 1 prior to delivery the membrane 44 is a single layer membrane folded over upon itself at the distal end region 43 whereupon it is engaged to the sheath 40. When the sheath 40 is retracted, the membrane 44 is pulled back off of the stent 30 as the outside fold 52 of the membrane rolls proximally on top of the inner fold 54 proximally until the entire membrane 44 is rolled off of the stent 30 such as is depicted in FIGS. 2-3.

During retraction of the membrane 44, the outer fold 52 of the membrane 44 will roll proximally on top of the inner fold 54 until the entire membrane 44 is rolled off of the stent 30 as depicted in FIG. 3. As discussed above in some embodiments a lubricant or other fluid 62 may be provided within the lumen 60 to encourage the rolling action of the folds 52 and 54 and/or separate the folds. The fluid 62 may be any type of "inflation fluid" such as may be utilized in balloon catheters which are known, and/or may be any sort of biocompatible fluid or lubricant such as is described in U.S. Pat. No. 5,693, 034, the entire content of which is incorporated herein by reference. In some embodiments fluid 62 is a liquid.

In some embodiments a hub, flange, protrusion(s), marker or other member 70 and 72 may be positioned proximally and/or adjacent to the stent receiving region 24. In some embodiments member 72 may also be provided with a diameter sufficiently greater than the diameter of the stent in the reduced state, to thereby prevent the stent from being inadvertently displaced in the proximal direction. Alternatively, the stent 30 may be crimped onto, or disposed about, one or more of the members 70 and/or 72, and/or the catheter 20 may be provided any of the variety of stent retaining mechanisms that are known. Members 70 and/or 72 may also include any known or later developed type of fixation system for reducing the likelihood of stent displacement prior to and/or during deployment.

Members 70 and/or 72 may be configured to be detectable by imaging modalities such as X-Ray, MRI or ultrasound. In some embodiments at least a portion of one or both members is at least partially radiopaque.

Figure 4:
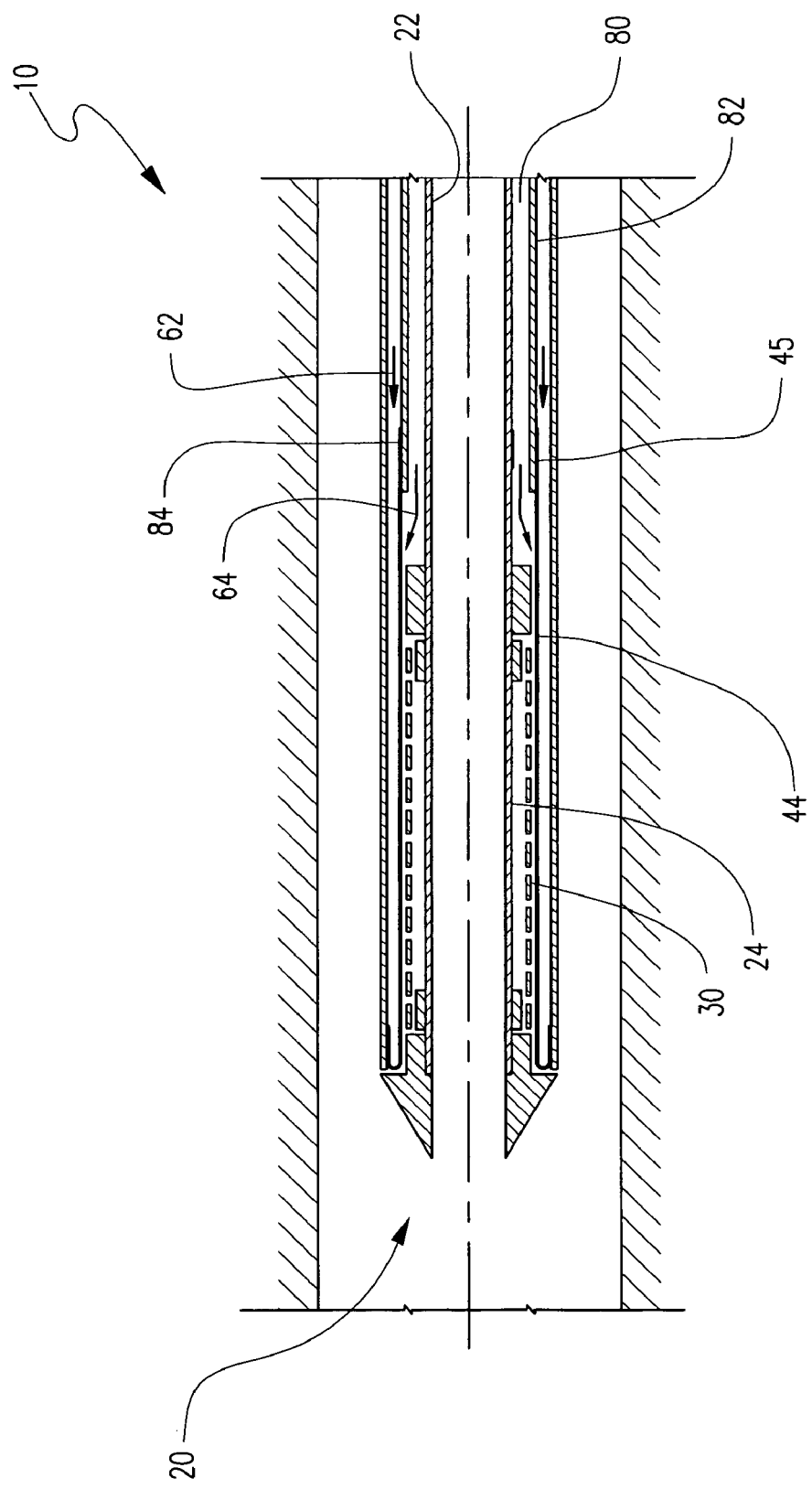
FIG. 4 is a longitudinal cross-sectional view of an alternative embodiment of the invention.

Turning now to the embodiment depicted in FIG. 4, in the embodiment shown, the catheter 20 is provided with a secondary lumen 80 which is formed between an intermediate shaft or mid-shaft 82 and the inner shaft 22 proximal to the stent receiving region 24. In this embodiment, the proximal end region 45 of the membrane 44 is engaged to a distal portion 84 of the mid-shaft 82. This modified system 10 provides a secondary lumen 80 which extends into the stent receiving region 24 of the catheter 20 which underlies the membrane 44. The secondary lumen 80 provides a flush path through which a fluid 64 may be transported to the stent receiving region 24 during or prior to delivery of the stent 30. Fluid 64 may be similar or different than fluid 62.

Flushing the stent receiving region 24 prior to delivery of the stent 30 and/or prior to use of the device 10 will not only purge the region 24 of air but will also act to reduce frictional engagement of the stent 30 and the membrane 44 prior to and/or during retraction of the membrane 44. Flushing can also be used to hydrate the shaft walls and/or the stent.

Figure 5:
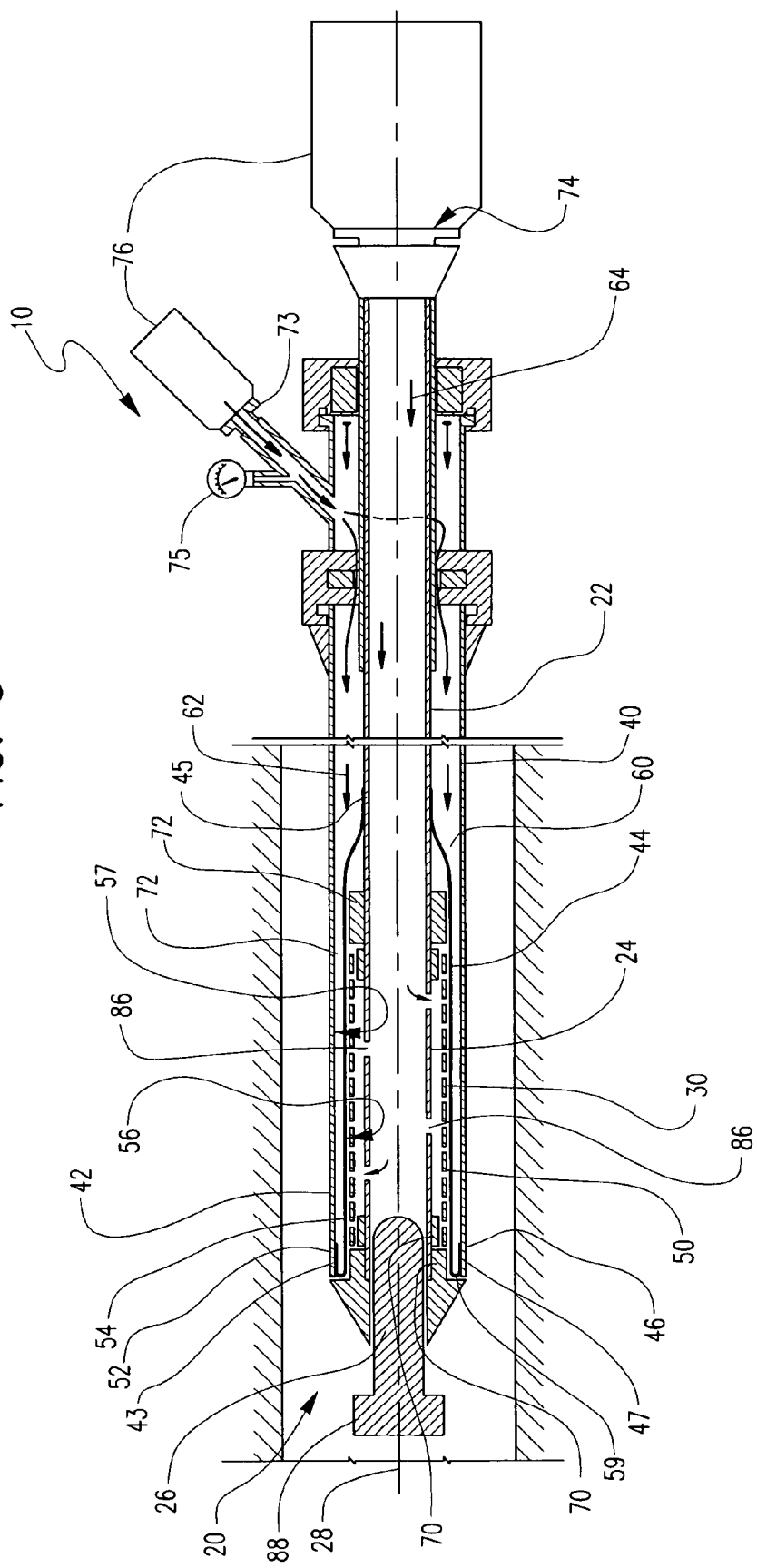
FIG. 5 is a longitudinal cross-sectional view of an alternative embodiment of the invention.

In some embodiments, a system 10 of the type shown in FIGS. 1-3 may also be provided with a flush path for flushing the stent receiving region 24 of the catheter 20 prior to use. In at least one embodiment, an example of which is depicted in FIG. 5, a flush path is defined by the guidewire lumen 26 and one or more holes or ports 86 through the stent receiving region 24 of the catheter shaft 22. Ports 86 provide fluid communication between the guidewire lumen 26 and the stent receiving region 24. By blocking or plugging the distal end of the guidewire lumen 26 with a shipping mandrel or other device 88, fluid 64 injected under pressure into the guidewire lumen 26 at the proximal end region 74 of the catheter 20 will be forced through the ports 86 to flush the stent receiving region 24. In some embodiments the ports 86 may be configured as a one-way valve to allow fluid to exit the guidewire lumen 26 but not re-enter.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
   a catheter, the catheter having a catheter shaft, a portion of the catheter shaft defining a stent receiving region;
   a sheath, the sheath being disposed about the catheter shaft and being longitudinally moveable relative thereto, a distal portion of the sheath defining a stent retaining region, the sheath being moveable between an extended position and a retracted position, in the extended position the retaining region being disposed about the stent receiving region, in the retracted position the sheath being removed from the stent receiving region;
   a membrane, a distal region of the membrane being engaged to a distal portion of the sheath, a proximal region of the membrane being engaged to a portion of the catheter shaft proximal of the stent receiving region, in the extended position the membrane being positioned between the catheter shaft and the sheath and a portion of the membrane being disposed about at least a portion of the stent receiving region, in the retracted position the membrane being removed from about the at least a portion of the stent receiving region; and
   a fluid chamber, the fluid chamber having a proximal region and a distal region, the proximal region being defined by the catheter shaft and the sheath, in the extended position the distal portion of the fluid chamber being defined by the membrane and the sheath and in the retracted position the distal portion of the fluid chamber being defined by said membrane.

2. The medical device of claim 1 wherein the fluid chamber is in fluid communication with a fluid port, the fluid port constructed and arranged to receive a fluid into the fluid chamber.

3. The medical device of claim 1 further comprising a stent, the stent being expandable from a reduced state to an expanded state, in the reduced state the stent having a diameter less than the diameter in the expanded state, when the sheath is in the extended position the stent is in the reduced state disposed about the stent receiving region.

4. The medical device of claim 3 further comprising at least one stent securing member, the at least one stent securing member being engaged to the catheter shaft and being positioned adjacent the stent receiving region, wherein in the reduced state the stent is engaged to the stent securing member.

5. The medical device of claim 3 wherein the stent is at least partially radiopaque.

6. The medical device of claim 3 wherein the stent is configured to be detectable by at least one of the following detection modalities: X-Ray, MRI, ultrasound, and any combination thereof.

7. The medical device of claim 3 wherein in the extended position the portion of the membrane is disposed about the stent.

8. The medical device of claim 7 wherein at least a portion of the stent comprises at least one therapeutic agent.

9. The medical device of claim 8 wherein the at least one therapeutic agent is a coating selected from at least one member of the group consisting of non-genetic therapeutic agents, genetic therapeutic agents, cellular material, and any combination thereof.

10. The medical device of claim 9 wherein the at least one therapeutic agent comprises at least one polymer agent.

11. The medical device of claim 7 wherein in the extended state the distal end portion of the membrane is folded to define an inside fold, an outside fold and a continuous bend region therebetween, the outside fold being engaged to the distal portion of the sheath, the inside fold being positioned between the outside fold and the stent.

12. The medical device of claim 11 wherein when the sheath is retracted from the extended state to the retracted state the outside fold is drawn in a proximal longitudinal direction over the inside fold along the continuous bend region until the entire membrane is rollingly retracted from about the stent.

13. The medical device of claim 11 further comprising a fluid the fluid positioned between the inside fold and the outside fold.

14. The medical device of claim 1 further comprising at least one stent securing member, the at least one stent securing member being engaged to the catheter shaft and being positioned adjacent the stent receiving region.

15. The medical device of claim 14 wherein the at least one stent securing member comprises a proximal stent securing member and a distal stent securing member, the proximal stent securing member being positioned adjacent a proximal end of the stent receiving region and the distal stent securing member being positioned adjacent a distal end of the stent receiving region.

16. The medical device of claim 14 wherein the at least one stent securing member is at least partially radiopaque.

17. The medical device of claim 16 wherein the at least one stent securing member is configured to be detectable by at least one of the following detection modalities: X-Ray, MRI, ultrasound, and any combination thereof.

18. The medical device of claim 1 wherein the sheath is at least partially constructed of at least one polymer of the group consisting of poly(ether-block-amide), poly(ether-ester), Nylon, PTFE, and any combinations thereof.

19. The medical device of claim 1 wherein the membrane is at least partially constructed of at least one material of the group consisting of poly(ether-block-amide), PET, Nylon, POC, Polyurethane, and any combinations thereof.

* * * * *